United States Patent
Lee et al.

(10) Patent No.: US 10,722,526 B2
(45) Date of Patent: Jul. 28, 2020

(54) PHARMACEUTICAL COMPOSITIONS FOR RADIOPROTECTION OR RADIOMITIGATION AND METHODS FOR USING THEM

(71) Applicant: KOREA INSTITUTE OF RADIOLOGICAL & MEDICAL SCIENCES, Seoul (KR)

(72) Inventors: Yoon Jin Lee, Seoul (KR); Hae June Lee, Seoul (KR); Jae Kyung Nam, Seoul (KR); A Ram Kim, Gyeonggi-do (KR); Kyeng Jung Kim, Seoul (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 0 days.

(21) Appl. No.: 15/780,051

(22) PCT Filed: Dec. 23, 2015

(86) PCT No.: PCT/KR2015/014204
§ 371 (c)(1),
(2) Date: May 30, 2018

(87) PCT Pub. No.: WO2017/094956
PCT Pub. Date: Jun. 8, 2017

(65) Prior Publication Data
US 2018/0360847 A1 Dec. 20, 2018

(30) Foreign Application Priority Data
Dec. 1, 2015 (KR) .................. 10-2015-0170111

(51) Int. Cl.
| | | |
|---|---|---|
| *A61K 31/565* | (2006.01) | |
| *A61P 11/00* | (2006.01) | |
| *A61P 17/00* | (2006.01) | |
| *A61P 9/00* | (2006.01) | |
| *A61K 47/12* | (2006.01) | |
| *A61K 9/00* | (2006.01) | |

(52) U.S. Cl.
CPC ............ *A61K 31/565* (2013.01); *A61K 47/12* (2013.01); *A61P 9/00* (2018.01); *A61P 11/00* (2018.01); *A61P 17/00* (2018.01); *A61K 9/0019* (2013.01); *A61K 9/0053* (2013.01)

(58) Field of Classification Search
CPC .. A61K 31/565; A61K 9/0019; A61K 9/0053; A61K 31/56
See application file for complete search history.

(56) References Cited

FOREIGN PATENT DOCUMENTS

| KR | 1020060012618 | 2/2006 |
| KR | 1020070011564 | 1/2007 |
| KR | 1020120076223 | 7/2012 |
| KR | 1020160038637 | 4/2016 |

OTHER PUBLICATIONS

Choi et al. Clin Cancer Res 2015, 21 (16), 3716-3726, published on line Apr. 24, 2015.*
Milliat et al. The American Journal of Pathology 2006, 169 (4), 1484-1495.*
Tofovic et al., "2-Methoxyestradiol Attenuates Bleomycin-Induced Pulmonary Hypertension and Fibrosis in Estrogen-Deficient Rats" Vascul Pharmacol. 2009, v 51 (2-3), p. 190-197.
Choi, S, H. etc, A hypoxia-induced vascular endothelial-to-mesechymal transition in development of radiation-induced pulmonary fibrosis. Clinical Cancer Research, 2015, 8, 21, 16, 3716-3726.
Xie et al., "Expression and significance of HIF-1a in pulmonary fibrosis induced by paraquat" Experimental Biology and Medicine, 2013, v 238, p. 1062-1068.
Leask et al., "TGF-beta signaling and the fibrotic response" FASEB, 2004, p. 816-827.
Ochoa et al., "Pneumonitis and pulmonary fibrosis in a patient receiving adjuvant docetaxel and cyclophosphamide for stage 3 breast cancer: a case report and literature review" Journal of Medical Case Reports, 2012, v 6, n 413, p. 1-6.
Xin M et al., "An efficient, practical synthesis of 2-methoxyestradiol" Steroids. Jan. 2010, v 75, p. 53-56.
Hou Y et al., "A Short, Economical Synthesis of 2-Methoxyestradiol, an Anticancer Agent in Clinical Trials" J Org Chem. Aug. 21, 2009, v 74, p. 6362-6364.
DuPage et al., "Conditional mouse lung cancer models using adenoviral or lentiviral delivery of Cre recombinase" Nature Protocols, v 4, n 7, p. 1064-1072.
Mousas et al., "Pulmonary Radiation Injury" Chest, 1997, v 111, p. 1061-1076.
Crooks et al., "Inflammation and Pulmonary Fibrosis" Hull York Medical School and Hull and East Yorkshire Hospitals NHS Trust, UK.
Johnston CJ et al., "Radiation-induced pulmonary fibrosis: examination of chemokine and chemokine receptor families" Radiat Res. Mar. 2002, v 157, n 3, p. 256-265.
Ghobadi et al., "Lung irradiation induces pulmonary vascular remodelling resembling pulmonary arterial hypertension" Thorax, Dec. 26, 2011.
Walters et al., "Mouse Models of Bleomycin-Induced Pulmonary Fibrosis" Current Protocols in Pharmacology, Mar. 2008, Supplement 40, 5.46.1-5.46.17.

(Continued)

*Primary Examiner* — Irina Neagu
(74) *Attorney, Agent, or Firm* — Greer, Burns & Crain, Ltd.; Gregory P. Einhorn

(57) ABSTRACT

The present invention relates to a pharmaceutical composition for radioprotection or radiomitigation with respect to radiation-induced damage, the composition comprising a compound of Formula 1, or a pharmaceutically acceptable salt thereof or a solvate thereof.

16 Claims, 4 Drawing Sheets

(56) References Cited

OTHER PUBLICATIONS

Iyer et al., "Effects of Pirfenidone on Procollagen Gene Expression at the Transcriptional Level in Bleomycin Hamster Model of Lung Fibrosis" The Journal of Pharmacology and Experimental Therapeutics, Mar. 25, 1998, v 259, n 1, p. 211-218.

\* cited by examiner

PHARMACEUTICAL COMPOSITIONS FOR RADIOPROTECTION OR RADIOMITIGATION AND METHODS FOR USING THEM

This application is a national phase application claiming benefit of priority under 35 U.S.C. § 371 to International (PCT) Patent Application serial number PCT/KR2015/014204, filed 23 Dec. 2015, which claims benefit of priority to Korean Patent Application No. 10-2015-0170111, filed 1 Dec. 2015. The aforementioned applications are expressly incorporated herein by reference in their entirety and for all purposes.

TECHNICAL FIELD

The present invention relates to a pharmaceutical composition for radioprotection or radiomitigation, more specifically, to a pharmaceutical composition for protecting a living body from any damage that could be induced by radiation exposure including pulmonary fibrosis.

BACKGROUND ART

There are various instances where the living body is damaged by radiation exposure, such as exposure to radiation in industrial sites where radiation is handled, adverse effects on normal tissues upon treatment with radiation, etc. In particular, since the terrorist attack in the US on Sep. 11, 2001, and the nuclear disaster in Fukushima, Japan in 2011, national research has been intensively conducted as a countermeasure against further radiation incidents. Since 9/11, the Armed Forces Radiobiology Research Institute (AFRRI) under the US Department of Defense has been actively promoting research on overcoming biological side effects due to radiation and research on biological defense mechanisms, and the National Institute of Allergy and Infectious Diseases (NIAID) is heavily investing in the development of medical countermeasures for radiological and nuclear attacks with the establishment of the Centers for Countermeasures Against Radiation (CMCR). Further, the development of new efficient medical techniques for measuring, diagnosing, or treating radiation exposure damage and research on the use of techniques in improving treatment efficiency technology through protection of normal tissue during radiotherapy are in progress. Drugs for radiation exposure are classified into: radioprotectants, which are applied prior to radiation exposure; mitigators, which are applied during or a short time after radiation exposure and before clear signs of symptoms become manifest; and therapeutic agents, which are applied after clear signs of symptoms become manifest due to radiation exposure.

Amifostine (Ethyol R), an aminothiol derivative, is a representative example of a radioprotectant. Aminothiols are chemical derivatives of cysteine, and act as a radioprotectant by functioning as a free radical scavenger. Amifostine (WR-2721) was developed by the Walter Reed Army Institute of Research program, and more than 4,000 aminothiol derivative compounds have been developed and tested.

Amifostine protects normal tissue, but not solid tumors, from radiation, and thus is used in the treatment of tumor radiotherapy. Further, amifostine is the first FDA-approved drug for xerostomia, the most frequently occurring side effect of radiotherapy for head and neck cancers. It is currently used for patients undergoing chemotherapy; however, it has been used with limitations as it is accompanied by side effects of low anti-oxidation efficacy, nausea, vomiting, low blood pressure, etc.

Pulmonary fibrosis due to exposure to radiation may be caused by an accident, but mostly occurs as a chronic side effect of radiotherapy for cancer. In this case, it reduces a cure rate of radiotherapy. As radiotherapy technology develops, the survival rate of the patients with cancer who have received radiotherapy has recently been increasing; however, it has been a serious issue that the pulmonary fibrosis which occurs as a side effect due to radiation degrades patients' quality of life. Recently, with the development of radiotherapy equipment and software along with the evolution of radiobiological concepts, a radiotherapy technique capable of effectively controlling only the cancer lesion while protecting normal tissue through one to several radiotherapy treatments (around five times) has been developed, but its use is as yet limited depending on the stage of cancer progression, the site of cancer onset, etc.

Despite the development in radiotherapy technology, a side effect such as pulmonary fibrosis, which inevitably occurs due to radiotherapy, is common in patients receiving radiotherapy to the thorax. Pneumonia develops in 10% to 15% of those who have received radiotherapy to the thorax for lung cancer, breast cancer, or Hodgkin's lymphoma 2 to 3 months after the radiotherapy, which is followed by a chronic side effect of fibrosis 6 months later. Such developed pulmonary fibrosis is maintained for 2 years and leads to pulmonary hypofunction as well as pain and discomfort of living for patients (Non-Patent Document 1). Accordingly, there is an urgent need for the discovery and development of a drug inhibiting pulmonary fibrosis.

There has been a report that TGF-b(SMAD), α-SMA, endothelin-1, etc. increase as markers for predicting pulmonary artery fibrosis (Non-Patent Documents 2 and 3). Immunosuppressants, such as steroids, cytotoxic drugs, etc., are mainly used in the treatment of pulmonary fibrosis, and steroids are preferentially used. A combination therapy of a steroid and azathioprine or cyclophosphamide is currently used as a therapeutic agent for pulmonary fibrosis due to exposure to radiation (Non-Patent Document 4). However, there is no clear evidence that such therapy would improve patients' survival rate or quality of life. Various fibrosis inhibitors have been experimented with on animals and a small group of patients, but no prominent effects have been proven.

Accordingly, there is a need for the development of a composition for radioprotection or radiomitigation capable of preventing or mitigating radiation-induced tissue damage including pulmonary fibrosis caused by radiation.

PRIOR ART

Non-Patent Document (Document 1) Benjamin M et al., Chest. 111(4):1061-1076. 19

(Document 2) Xie H et al., Exp Biol Med (Maywood):238 (9):1062-8. 2013.

(Document 3) Andrew L et al., FASEB: 816-827. 2004

(Document 4) Ochoa et al., Journal of Medical Case Reports, 6:413.2012

DISCLOSURE

Technical Problem

An object of the present invention is to develop a drug that can be used as radioprotective and radiomitigative agents.

Another object of the present invention is to provide a radioprotection or radiomitigation method comprising administering the drug.

Technical Solution

An aspect of the present invention provides a pharmaceutical composition for radioprotection or radiomitigation, comprising a compound of Formula 1 below, or a pharmaceutically acceptable salt thereof or a solvate thereof:

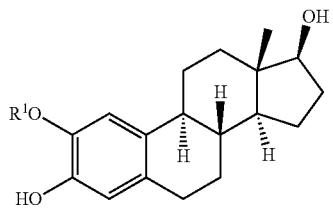

[Formula 1]

wherein, in Formula 1,
R$^1$ is hydrogen or C$_{1-3}$ alkyl.

Another aspect of the present invention provides a radioprotection or radiomitigation method comprising administering a therapeutically effective amount of a compound of Formula 1 below, or a pharmaceutically acceptable salt thereof or a solvate thereof to an animal excluding humans:

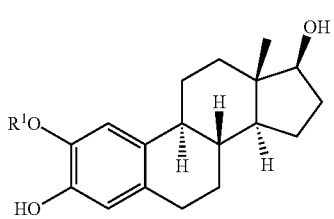

[Formula 1]

wherein, in Formula 1,
R$^1$ is hydrogen or C$_{1-3}$ alkyl.

Advantageous Effects

The compound of Formula 1 or a pharmaceutically acceptable salt thereof or a solvate thereof according to the present invention appears to be able to prevent or mitigate any radiation-induced damage including vascular injury, skin damage, tissue inflammation, or tissue fibrosis due to radiation exposure by radioprotective and radiomitigative actions. Accordingly, the pharmaceutical composition according to an aspect of the present invention is expected to be effectively used in protection or mitigation of any radiation-induced damage including vascular injury, skin damage, tissue inflammation, or tissue fibrosis due to radiation exposure.

Additionally, the compound of Formula 1 or a pharmaceutically acceptable salt thereof or a solvate thereof according to the present invention appears to be able to prevent or mitigate pulmonary fibrosis due to radiation exposure by radioprotective and radiomitigative actions. Accordingly, the pharmaceutical composition according to an aspect of the present invention is expected to be effectively used in protection or mitigation of pulmonary fibrosis due to radiation exposure. Furthermore, as it can be effectively used for pulmonary fibrosis, which may appear as a side effect of radiotherapy for lung cancer, breast cancer, or Hodgkin's lymphoma, the pharmaceutical composition of an aspect of the present invention is preferable in that it can overcome the problems of radiotherapy for cancer.

DESCRIPTION OF THE DRAWINGS

<Description of the Figures>
No.IR: control group (group with no irradiation)
IR: group with irradiation
IR+pre-treatment2Me: group with irradiation and pre-treatment with 2-methoxyestradiol

BEST MODE

Figure 1:
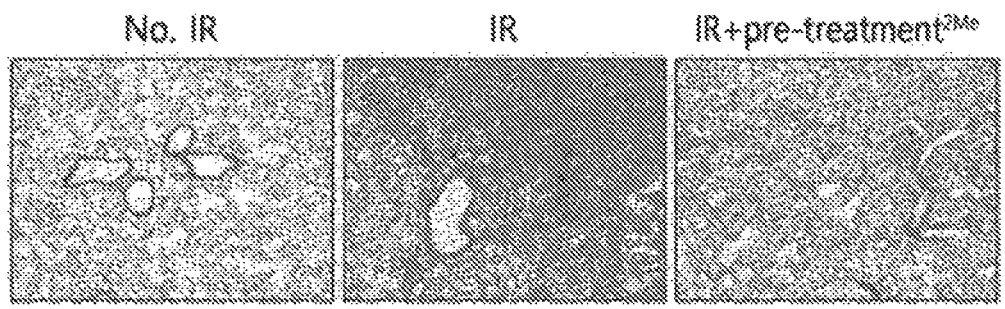
FIG. 1 shows images of the results of inflammation at the site of tissue damage measured by H&E staining after a radiation dose of 90 Gy was delivered to the lung of a mouse model untreated or treated with 60 mg/kg 2-methoxyestradiol 1 hour before irradiation.

Hereinbelow, the present invention will be described in more detail.

All technical terms used herein, unless otherwise defined, have the meaning as commonly understood by one of ordinary skill in the art to which this invention pertains. All references, including publications, patent documents, and non-patent documents cited herein are incorporated herein in their entirety by reference.

The research showed that the compound of Formula 1 below, represented by 2-methoxyestrodiol, significantly decreases tissue damage, vascular injury, and skin damage, which are induced by radiation exposure when administered before and after the radiation exposure. Additionally, the compound of Formula 1 below not only reduces the degree of increase in the amounts of collagen deposited in the alveolar wall and protein related to pulmonary fibrosis, which occurs during radiation-induced pulmonary fibrosis, but also increases VE-cadherin, an expression protein specific to normal pulmonary artery endothelial cells, which decrease during pulmonary fibrosis. Accordingly, the compound of Formula 1 was confirmed to be able to protect biotissue from various kinds of damage including pulmonary fibrosis, tissue damage, vascular injury, and skin damage, which are induced by radiation.

An aspect of the present invention provides a pharmaceutical composition for radioprotection or radiomitigation with respect to radiation-induced damage, comprising the compound of Formula 1 below, or a pharmaceutically acceptable salt thereof or a solvate thereof:

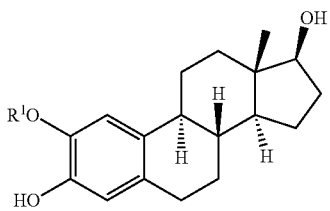

[Formula 1]

wherein, in Formula 1,
$R^1$ is hydrogen or $C_{1-3}$ alkyl.

According to an exemplary embodiment, the compound of Formula 1 above is 2-methoxyestradiol where $R^1$ is methyl.

The compound of Formula 1 can be prepared using conventional knowledge known in the field of organic chemistry, or a commercially available product thereof can be purchased for use. For example, it can be manufactured using the method disclosed in Xin M et al., An efficient, practical synthesis of 2-methoxyestradiol. Steroids. 2010 January; 75(1):53-6.; or Hou Y et al., A Short, Economical Synthesis of 2-Methoxyestradiol, an Anticancer Agent in Clinical. J Org Chem. 2009 Aug. 21; 74(16):6362-4).

The pharmaceutically acceptable salt thereof or solvate of the compound of Formula 1 above can be appropriately manufactured or selected using knowledge known in the technical field of organic chemistry by one of ordinary skill in the art. In a specific embodiment, the solvate is a hydrate.

The pharmaceutically acceptable salt may be present as an acid addition salt, wherein the compound of Formula 1 forms a salt with a free acid. The compound of Formula 1 may form an acid addition salt according to a conventional method known in the corresponding technical field. An organic or inorganic acid can be used as the free acid, wherein hydrochloric acid, bromic acid, sulfuric acid, or phosphoric acid can be used as the inorganic acid; and citric acid, acetic acid, lactic acid, tartaric acid, valeric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, or aspartic acid can be used as the organic acid.

As used herein, the term "radioprotection" refers to suppression or alleviation of any radiation-induced damage induced by radiation exposure by applying to the living body before the radiation exposure.

As used herein, the term "radiomitigation" refers to suppression or alleviation of any radiation-induced damage induced by radiation exposure by applying to the living body immediately within a short period of time after the radiation exposure before any clinical sign becomes clearly manifest. The term "short period of time" refers to a period of time that enables the suppression or alleviation of any radiation-induced damage by applying a substance before any clinical sign due to the radiation exposure becomes clearly manifest. In a specific embodiment, the short period of time refers to within 36 hours, 24 hours, or 12 hours after the radiation exposure, but is not limited thereto.

The radiation-induced damage refers to any damage to the living body induced by radiation exposure, and includes vascular injury, skin damage, tissue inflammation, or tissue fibrosis due to radiation exposure, but is not limited thereto.

The radiation-induced damage also includes pulmonary fibrosis due to radiation exposure. The pulmonary fibrosis may be any pulmonary fibrosis caused by various reasons. In a specific embodiment, the pulmonary fibrosis is caused by radiation exposure. Additionally, in a specific embodiment, the pulmonary fibrosis refers to a side effect of radiotherapy, which is caused by radiation exposure in a normal tissue during the radiotherapy for a cancer. The radiotherapy for cancers, which may induce the pulmonary fibrosis, includes radiotherapy for lung cancer, breast cancer, or Hodgkin's lymphoma, but is not limited thereto.

From an experiment of suppressing tissue damage due to radiation, the compound of Formula 1 was shown to be effective in protecting and alleviating tissue damage, including vascular injury and skin damage. More specifically, vascular changes inside the skin were observed after radiation exposure on the thorax of mice, and as a result, the group (IR+pre-treatment) which was administered the compound of Formula 1 before the radiation and that (IR+post-treatment) which administered the compound of Formula 1 after the radiation showed a significant decrease in the inflammation and fibrosis of lung tissue compared to the untreated group (IR) (see Example 1). Additionally, vascular changes inside the skin were observed after radiation exposure on the thorax of mice, and as a result, the group (IR+pre-treatment) which administered the compound of Formula 1 before the radiation and that (IR+post-treatment) which administered the compound of Formula 1 after the radiation showed a significant decrease in the skin and vascular damage compared to the untreated group (IR) (see Example 2). Further, the compound of Formula 1, from an experiment of suppressing tissue damage due to radiation, was shown to be effective in protecting and alleviating tissue damage including vascular injury and skin damage. Further, the infiltration of the inflammatory cells in the skin tissue was observed after radiation exposure on the thorax of mice, and as a result, the group (IR+pre-treatment) which administered the compound of Formula 1 before the radiation and that (IR+post-treatment) which administered the compound of Formula 1 after the radiation showed a significant decrease in the number of the inflammatory cells that infiltrated the skin tissue compared to the untreated group (IR) (see Example 3). Accordingly, the compound of Formula 1 was confirmed to have radioprotective and radiomitigative effects on radiation-induced tissue damage including tissue inflammation, tissue fibrosis, vascular injury, and skin damage.

Further, the compound of Formula 1 not only reduces the degree of increase in the amounts of collagen deposited in the alveolar wall and protein related to pulmonary fibrosis, which occurs during pulmonary fibrosis, but also increases VE-cadherin, an expression protein specific to normal pulmonary artery endothelial cells, which decrease during pulmonary fibrosis. During pulmonary fibrosis due to radiation, pulmonary artery endothelial cells lose their original properties due to radiation, and another type of cellular characteristic, in particular, an increase in the amount of proteins related to fibrosis cells, is observed. This can be easily distinguished by quantitative changes of proteins related to endothelial cells and pulmonary fibrosis. The present invention revealed from the experiment that when pre-treated with 2-methoxyestradiol, the expression of VE-cadherin, an expression protein specific to vascular endothelial cells that reduces due to radiation, significantly increases in HPAECs compared to the no-irradiation group, and the activation and quantitative increase of phalloidin, CA-9, p-SMAD2/3, and α-SMA, pulmonary fibrosis-related proteins that increase due to radiation, significantly reduces compared the non-treatment group (Examples 4 and 6). Additionally, the present inventors confirmed that symptoms of pulmonary fibrosis such as collagen increase appear on the inner wall of the aorta upon irradiation of the lung of actual experimental animals (mice), and the group administered with 2-methoxyestradiol showed a significant reduction in the degree of increase in the amounts of collagen compared with the untreated group (Example 5). Further, the present inventors confirmed that symptoms of pulmonary fibrosis such as collagen increase appear on the inner wall of the aorta, although the size of lung cancer decreases after radiotherapy in the mouse model with lung cancer, and the group administered with 2-methoxyestradiol showed a significant reduction in the degree of increase in the amounts of collagen compared with the untreated group (Example 7). Accordingly, such experiment results show that the compound of Formula 1, such as 2-methoxyestradiol, can significantly reduce symptoms of pulmonary fibrosis which appear during the radiotherapy for cancer or when exposed to radiation.

The pharmaceutical composition for radioprotection or radiomitigation according to the present invention may be formulated in conventional pharmaceutical formulations known in the art. The pharmaceutical formulations include oral preparations, injections, suppositories, transdermal drugs, and pernasal drugs, but are not limited thereto and may be formulated and administered in any other formulation. Preferably, the pharmaceutical formulations may be formulated in oral preparations or injections. The formulations for oral administration may be formulated as liquid formulation, suspension, powders, granules, tablets, capsules, pills, or extracts.

When formulating the pharmaceutical composition in each formulation, a pharmaceutically acceptable carrier or additive necessary for the preparation thereof can be added.

When formulating the pharmaceutical composition in an oral preparation, at least one of a diluent, a lubricant, a binding agent, a disintegrant, a sweetener, a stabilizer, and a preservative can be selected and used as the carrier. As the additive, at least one of a flavor, vitamin, and antioxidant may be selected and used.

There is no limitation on the carrier and additive as long as they are pharmaceutically acceptable. Specifically, lactose, corn starch, soybean oil, microcrystalline cellulose, or mannitol is preferred as the diluent; magnesium stearate or talc is preferred as the lubricant; and polyvinyl pyrrolidone or hydroxypropylcellulose is preferred as the binding agent. Further, it is preferable that carboxymethylcellulose calcium, sodium starch glycolate, polacrilin potassium, or crospovidone be used as the disintegrant; white sugar, fructose, sorbitol, or aspartame be used as the sweetener; sodium carboxymethyl cellulose, beta-cyclodextrin, beeswax, or xanthan gum be used as the stabilizer; and methyl p-hydroxybenzoate, propyl p-hydroxybenzoate, or potassium sorbate be used as the preservative.

In addition to the above components, conventionally known additives such as natural aromatics (e.g., Japanese apricot aromatic, lemon aromatic, pineapple aromatic, and herb aromatic), natural coloring agents (e.g., natural fruit juice, chlorophyllin, and flavonoid), sweetening components (e.g., fructose, honey, sugar alcohol, and sugar), or acidifiers (e.g., citric acid and sodium citrate) may be used in combination in order to improve taste.

When formulating the pharmaceutical composition in an injection, it can be prepared according to a conventional method for preparing an injection known in the art. The injection according to the present invention may be in the form dispersed in a sterilized medium, such that the injection may be used as it is when administered to a patient, or may be in the form which is dispersed to be at a suitable concentration through the addition of distilled water for injection at the time of administration thereof.

Technologies required for such formulation and pharmaceutically acceptable carriers and additives are widely known to a person in the art of formulations, and one may refer to the Handbook of Pharmaceutical Excipients, $4^{th}$ edition, Rowe et al., Eds., American Pharmaceuticals Association (2003); Remington: the Science and Practice of Pharmacy, 20th edition, Gennaro, Ed., Lippincott Williams & Wilkins (2000); Remington's Pharmaceutical Sciences (19th ed., 1995), etc.

In order to obtain the radioprotective and radiomitigative effects, the pharmaceutical composition according to the present invention, as the compound of Formula 1, may be administered in divided doses so that the total amount of administration becomes about 0.1 mg/kg to 100 mg/kg, based on a standard adult. The amount of administration may be appropriately increased or decreased in accordance with the strength of the radiation inducing damage, the type and progress of the radiation-induced damage, the route of administration, gender, age, weight, etc.

Another aspect of the present invention provides a radioprotection or radiomitigation method for radiation-induced damage, comprising administering a therapeutically effective amount of a compound of Formula 1 below, or a pharmaceutically acceptable salt thereof or a solvate thereof to an animal:

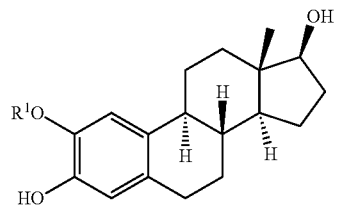

[Formula 1]

wherein, in Formula 1,
$R^1$ is hydrogen or $C_{1-3}$ alkyl.

The description regarding the pharmaceutical composition for radioprotection or radiomitigation according to an aspect of the present invention may be identically applied to the detail of the radioprotection or radiomitigation method for radiation-induced damage.

The animal may be any mammalian animal including humans, livestock, and pets, but is not limited thereto.

In a specific embodiment, the animal is a mammalian animal excluding humans.

Hereinafter, the present disclosure will be described in more detail with reference to the following exemplary embodiments. However, the following exemplary embodiments are provided for illustrative purposes only, and the scope of the present disclosure should not be limited thereto.

Experimental Method (1) Hematoxylin and Eosin Staining (H&E staining) of Body Tissues Tissue from a mouse was fixed in 10% neutral formalin for one day, and paraffin sections were prepared. The paraffin sections were then reacted for 5 minutes in each of xylene, and 95%, 90%, and 70% ethanol solutions in that order to deparaffinize the paraffin around the tissue. The tissue was then put into hematoxylin for 1 minute to stain the nucleus and washed with running water for 10 minutes, followed by dipping in eosin for 30 seconds to stain the cytoplasm. The tissue was then dipped in 50%, 70%, 90%, and 95% ethanol, and xylene in that order, and a drop of a mounting solution was applied thereto. The tissue was covered with a cover slide and observed with a microscope (Carl Zeiss Vision).

(2) Immunohistochemistry (IHC)

Tissue from a mouse was fixed in 10% neutral formalin for one day, and paraffin sections were prepared. The paraffin sections were then reacted for 5 minutes in each of xylene, and 95%, 90%, and 70% ethanol solutions in that order to deparaffinize the paraffin around the tissue. For antigen activation, the tissue was immersed in 0.1 M citrate (pH 6.0) and brought to a boil for 30 minutes, followed by reacting with 3% hydrogen peroxide for 15 minutes. Meanwhile, the tissue was then reacted in phosphate based saline buffer (PBS, 0.1% triton x-100 included) including CD31 (abcam, 1:100 dilution) at 4° C. for 16 hours. After washing with PBS, secondary antibodies having biotin conjugated were diluted at 1:200 and incubated at room temperature for 30 minutes. Avidin biotin complex (ABC) was applied and incubated at room temperature for 30 minutes, and 3,3'-DAB(3,3'-diaminobenzidine) was added for color detection. Hematoxylin was used for counterstaining. The tissue was then dipped in 50%, 70%, 90%, and 95% ethanol, and xylene in that order, and a drop of a mounting solution was applied thereto. The tissue was covered with a cover slide and observed with a microscope (Carl Zeiss Vision).

(3) Culture of Cell Lines to Be Used

Human pulmonary artery endothelial cells (HPAEC) bought from Promocell were cultured in a culture chamber at a temperature of 37° C. under a 5% $CO_2$ condition using a medium including various growth factors necessary for growth of the vascular endothelial cell.

(4) Irradiation on HPAEC

HPAECs were plated in 3.5 cm, 6 cm, and 10 cm culture dishes and cultured in a $CO_2$ incubator at 37° C. so that the cells were 70% to 80% confluent. 2-Methoxyestradiol was selectively pre-treated according to the test groups. 10 Gy gamma rays ($^{137}Cs$) (Atomic Energy of Canada, LTd., Canada) were radiated at a dose of 3.81 Gy/min.

(5) Immunofluorescence of Cells

HPAECs were cultured on the cover slide, selectively pre-treated with 2-methoxyestradiolin according to test groups, and irradiated. HPAECs were then fixed in 10% neutral formalin for one day, and washed with phosphate buffered saline (PBS) before staining. After blocking with 2% *bovine* serum albumin (dissolved inPBS) before the first antibody reaction, VE-cadherin, hypoxia-inducible factor 1-alpha (HIF-1α), SMAD, p-SMAD2/3, and α-SMA antibodies, diluted at 1:100, were reacted at 4° C. for 16 hours. After washing with PBS, the second antibodies having fluorescent stains attached were diluted at 1:500 and reacted at 25° C. for 1 hour. The nuclei were stained with a fluorescent stain 4',6-diamidino-2-phenylindole (DAPI). After washing with PBS, a drop of glycerol was applied to attach the stained cells to the glass slide. The cells were observed with a confocal microscope.

(6) Protein Analysis Using Electrophoresis and Immune Response

After the cultured cells were irradiated, specimens in which the cells were dissolved in a solution of 150 mM sodium chloride, 40 mM Tris-Cl (pH 8.0), 0.1% NP-40 were prepared to observe intracellular proteins. Sodium dodecyl sulfate polyacrylamide gel electrophoresis (SDS-PAGE) was performed on the specimens, followed by Western blot analysis. The proteins separated by electrophoresis were transferred to a nitrocellulose membrane, and the amount of protein expression was analyzed using the immunoblotting method.

(7) Hematoxylin and Eosin Staining (H&E Staining) of Body Tissues

Tissue from a mouse was fixed in 10% neutral formalin for one day, and paraffin sections were prepared. The paraffin sections were then reacted for 5 minutes in each of xylene, and 95%, 90%, and 70% ethanol solutions in order to deparaffinize the paraffin around the tissue for staining. The tissue was then put into hematoxylin for 1 minute to stain the nucleus and washed with running water for 10 minutes, followed by dipping in eosin for 30 seconds to stain the cytoplasm. The tissue was then dipped in 50%, 70%, 90%, and 95% ethanol, and xylene in that order, and a drop of a mounting solution was applied thereto. The tissue was covered with a cover slide and observed with a microscope (Carl Zeiss Vision).

(8) Trichrome Staining of Body Tissues

Tissue from a mouse was fixed in 10% neutral formalin for one day, and paraffin sections were prepared. The paraffin sections were then reacted for 5 minutes in each of xylene, and 95%, 90%, and 70% ethanol solutions in that order to deparaffinize the paraffin around the tissue for staining. For antigen activation, the tissue was soaked in a 0.1 M citric acid solution (pH 6.0) and boiled.

The tissue was then reacted in Bouin's solution for 1 minute, Weigert's hematoxylin for 10 minutes, phosphotunstic/phosphomolydic acid for 10 minutes, aniline blue for 5 minutes, and 1% acetate for 1 minute in that order. After dehydration, the tissue was sealed with a cover glass, and observed with a confocal microscope.

Example 1

Effect of 2-methoxyestradiol on the Suppression of Radiation-Induced Tissue Damage A mouse was exposed to 90 Gy radiation on the thorax in a size of 3 mm. Lung tissue from the mouse model was fixed in 10% neutral formalin, and paraffin sections were prepared. Using the hematoxylin and eosin staining method, inflammatory reactions and fibrosis of the tissue were observed. The cell nuclei were stained in blue and the cytoplasm was stained in pink. One hour before the irradiation, the mouse model received an intraperitoneal injection of 60 mg/kg 2-methoxyestradiol. Two weeks after the irradiation, inflammatory reactions and fibrosis were observed using H&E staining at the site of tissue damage.

FIG. 1 shows the images of the results of inflammation at the site of tissue damage measured by H&E staining after a radiation dose of 90 Gy was delivered to the lung of a mouse model untreated or treated with 60 mg/kg 2-methoxyestradiol 1 hour before the irradiation.

According to FIG. 1, when compared with the normal tissue (No.IR) through the H&E staining, the 90 Gy irradiation group (IR) showed infiltration of inflammatory cells. Additionally, the tissue of the IR group showed fibrosis around the damaged vessels compared to that of the No.IR group. In contrast, the tissue of the mouse pre-treated with 2-methoxyestradiol (IR+pre-treatment2Me) showed significantly reduced cell infiltration and fibrosis around blood vessels compared to the untreated group (IR).

It can be understood from the result of FIG. 1 that the treatment with 2-methoxyestradiol significantly reduces tissue damage induced by radiation.

Example 2

Effect of 2-methoxyestradiol on Radiation-Induced In Vivo Vascular Injury

To observe whether tissue damage resulting from radiotherapy shows a vascular injury of skin, a C57BL/6 mouse was exposed to 20 Gy radiation on the thorax in a size of 7 mm. Skin was extracted from the mouse, and vascular changes inside the skin were observed. The group pre-treated with 2-methoxyestradiol (IR+pre-treatment2Me) received an intraperitoneal injection in an amount of 60 mg/kg 1 hour before the irradiation, and that post-treated with 2-methoxyestradiol (IR+post-treatment2Me) received an intraperitoneal injection in an amount of 60 mg/kg 24 hours after the irradiation.

Figure 2:
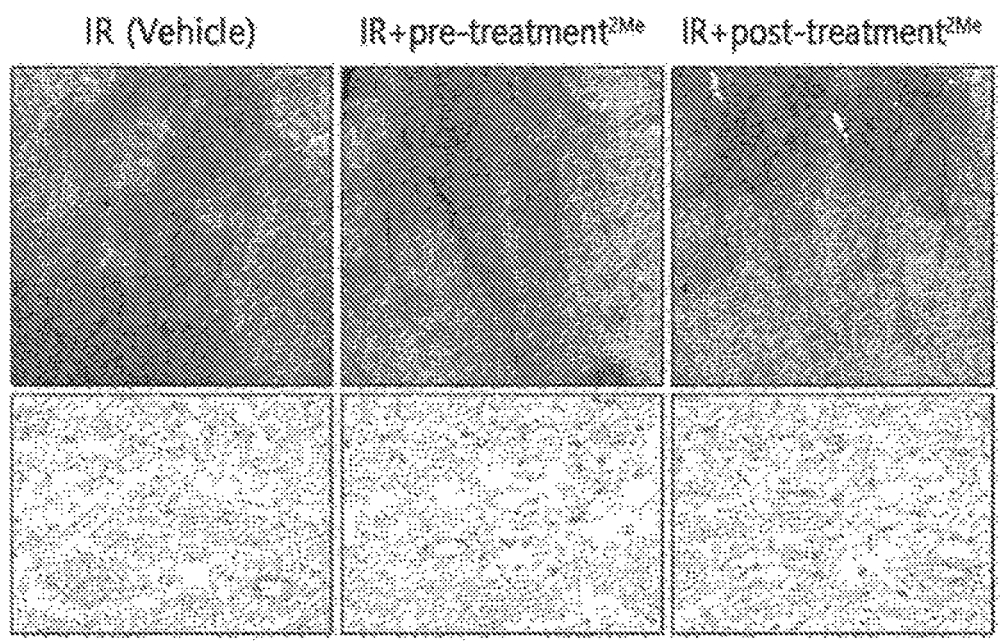
FIG. 2 shows the images of the vascular changes inside the skin of a mouse model pre-treated, post-treated, or untreated with 2-methoxyestradiol, along with irradiation of the thorax.

FIG. 2 shows the images of the vascular changes inside the skin of a mouse model pre-treated, post-treated, or untreated with 2-methoxyestradiol, along with irradiation of the thorax.

According to FIG. 2, the blood vessels of the skin of the irradiation group (IR) were observed to be unclear, while the group pre-treated (IR+pre-treatment2Me) or post-treated (IR+post-treatment2Me) with 2-methoxyestradiol showed a significant reduction in skin vascular injury compared to the untreated group (IR). According to FIG. 2, irradiation causes vascular injury on skin tissue, and the vascular injury caused by irradiation is significantly reduced upon pre- or post-treatment of 2-methoxyestradiol.

Example 3

Effect of 2-methoxyestradiol on Radiation-Induced In Vivo Skin Damage

To observe whether inflammatory responses and fibrosis of skin occur during tissue damage induced after radiotherapy, a C57BL/6 mouse was exposed to 20 Gy radiation on the thorax in a size of 7 mm. Skin was extracted from the mouse, and infiltration of inflammatory cells in the skin tissue was observed. The group pre-treated with 2-methoxyestradiol (IR+pre-treatment2Me) received an intraperitoneal injection in an amount of 60 mg/kg 1 hour before the irradiation, and that post-treated with 2-methoxyestradiol (IR+post-treatment2Me) received an intraperitoneal injection in an amount of 60 mg/kg 24 hours after the irradiation. The result 2 weeks after irradiation is shown in FIG. 3.

Figure 3:
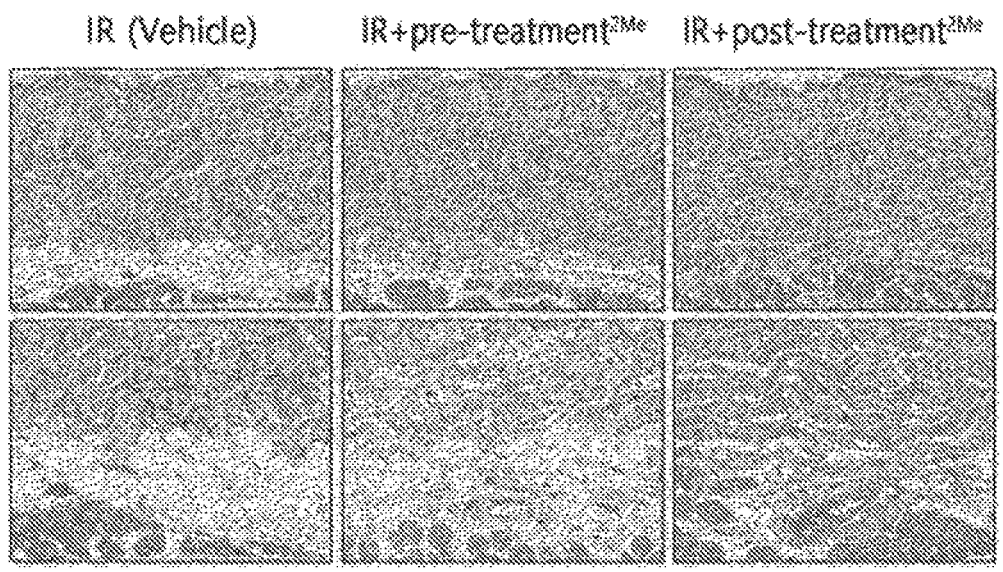
FIG. 3 shows the images of the infiltration of inflammatory cells inside the skin of a mouse model pre-treated, post-treated, or untreated with 2-methoxyestradiol, along with irradiation of the thorax.

FIG. 3 shows the images of the infiltration of inflammatory cells inside the skin of a mouse model pre-treated, post-treated, or untreated with 2-methoxyestradiol, along with irradiation on the thorax.

According to FIG. 3, inflammatory cells in the skin tissue of the irradiation group (IR) were observed to be quite infiltrated, while the group pre-treated (IR+pre-treatment2Me) or post-treated (IR+post-treatment2Me) with 2-methoxyestradiol showed a significantly reduced number of infiltrated inflammatory cells inside the skin tissue compared to the untreated group (IR). According to FIG. 3, irradiation causes tissue damage induced by the infiltration of inflammatory cells inside skin, and the skin tissue damage and inflammatory responses caused by irradiation are significantly reduced upon pre- or post-treatment of 2-methoxyestradiol.

Example 4

Suppression of Radiation-Induced Pulmonary Fibrosis Using Immunofluorescence Staining at the Cellular Level Human pulmonary artery endothelial cells which received 10 Gy radiation were fixed in 10% neutral formalin, and reacted with phalloidin, CA-9, and VE-cadherin antibodies. Then, fluorescent-labeled secondary immunoglobulins were used to stain CA9, phalloidin, and VE-cadherin in red, green, and white, respectively. The cell nuclei were stained in blue using DAPI. The group received 10 Gy radiation 12 hours after treating HPAECs with 10 ng/mL 2-methoxyestradiol. The result is shown in FIG. 4.

Figure 4:
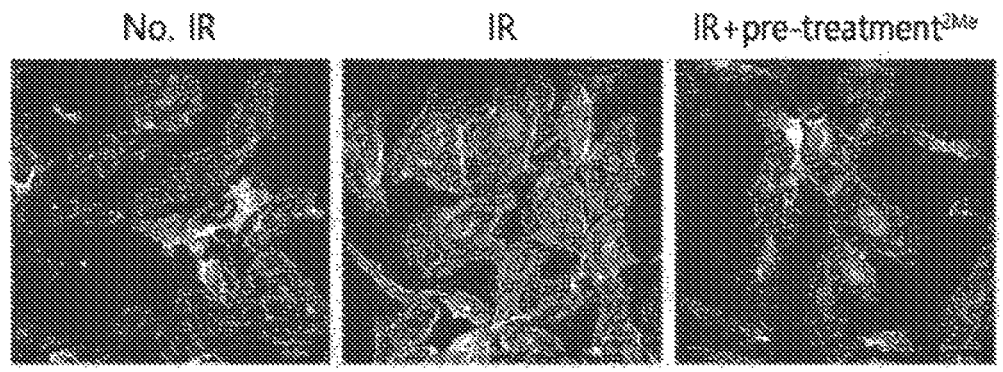
FIG. 4 shows the images of changes in the HPAEC shape and the increase and decrease of pulmonary fibrosis-related proteins, observed with a confocal microscope, after the HPAECs are untreated or treated with 2-methoxyestradiol followed by irradiation and fluorescence staining.

FIG. 4 shows the images of changes in the shape of the HPAECs and the increase and decrease of pulmonary fibrosis-related proteins, observed with a confocal microscope, after the HPAECs were untreated or treated with 2-methoxyestradiol followed by irradiation and fluorescence staining.

According to FIG. 4, VE-cadherin, as a protein present in the cell membrane of pulmonary artery endothelial cells, is shown in white in the image of the control group (No.IR). Meanwhile, the irradiation group (IR) showed a significant decrease in the white around the cell membrane. Phalloidin and CA-9, as proteins related to pulmonary fibrosis, were not stained in the control group, whereas they were stained in green and red, respectively, in the IR group. In contrast, the group pre-treated with 2-methoxyestradiol(IR+pre-treatment2Me) showed a significant increase in the white around the cell membrane, and a significant decrease of phalloidin and CA-9.

It can be understood from the result of FIG. 4 that the treatment with 2-methoxyestradiol significantly decreases symptoms related to pulmonary fibrosis, which is increased by irradiation of HPAECs, and suppresses cell membrane damage caused by irradiation.

Example 5

Suppression of Pulmonary Fibrosis in an Experimental Animal Model

To observe whether the symptoms of pulmonary fibrosis induced after radiotherapy include pulmonary fibrosis of vascular endothelial cells, a C57BL/6 mouse was exposed to 16 Gy radiation on the lung. The lung was extracted from the mouse, and collagen, a protein appearing on the cross-section of aorta during the fibrosis of pulmonary artery endothelial cell, was detected by trichrome staining. The group treated with 2-methoxyestradiol was intraperitoneally injected in an amount of 150 mg/kg 1 hour before irradiation. The result is shown in FIG. 5.

Figure 5A:
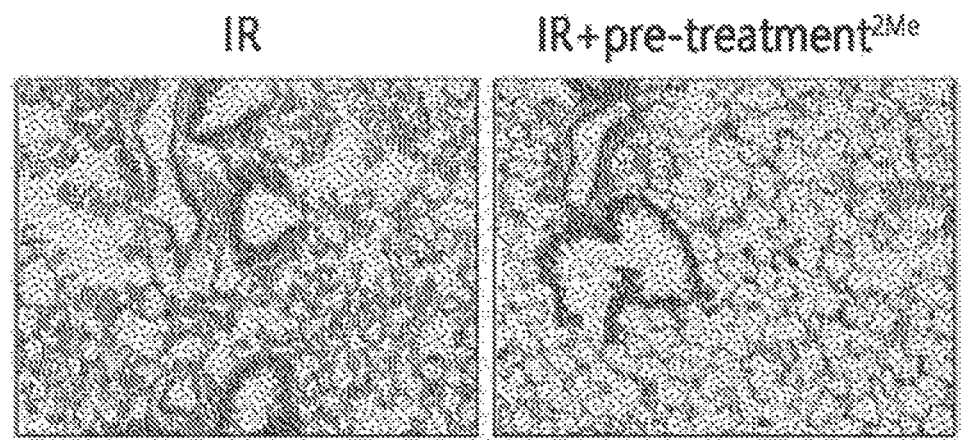
FIG. 5a is the images of the result of the trichrome staining of the collagens in the pulmonary artery endothelium of the mouse model untreated or treated with 2-methoxyestradiol and then irradiation of the lung.

FIG. 5a is the images of the result of the trichrome staining of the collagens in the pulmonary artery endothelium of the mouse model untreated or treated with 2-methoxyestradiol followed by irradiation of the lung.

Figure 5B:
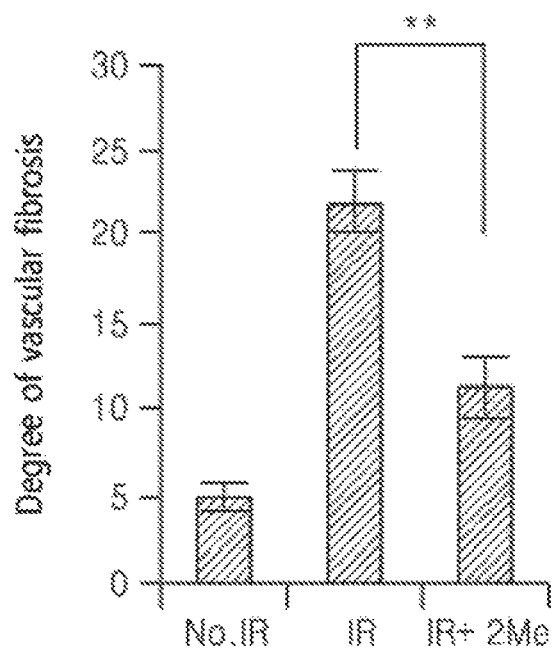
FIG. 5b is the graphs statistically showing the expression of the collagen, a molecule related to pulmonary fibrosis, using trichrome staining.

FIG. 5b is the graphs statistically showing the expression of the collagen, a molecule related to pulmonary fibrosis, using trichrome staining. Additionally, it is shown in terms of significance probability (**: P<0.01) that there is statistical significance in the effect of 2-methoxyestradiol between the experimental group in which fibrosis is increased by irradiation and that in which fibrosis is decreased by the 2-methoxyestradiol treatment.

According to FIG. 5, the blue color(collagen) in the aortic wall of the irradiation group (IR) was comparatively increased, whereas the control group with no irradiation (image not shown) showed almost no blue color, which represents stained collagen. Accordingly, it was confirmed that pulmonary fibrosis was induced by irradiation of the lung of the mouse. In contrast, the group pre-treated with 2-methoxyestradiol(IR+pre-treatment2Me) showed a significant decrease of the collagen stained in blue compared to the irradiation group (IR). The part observed blue is marked with a white square in FIG. 5a.

It can be understood from the result of FIG. 5 that 2-methoxyestradiol significantly suppresses fibrosis of HPAECs induced by radiation.

Example 6

Suppression of Radiation-Induced Pulmonary Fibrosis of HPAECs

In order to observe changes in the expression amount of the proteins related to HPAEC pulmonary fibrosis according to the concentrations of 2-methoxyestradiol (0.5 μM and 1 μM), the cultured HPAECs were pre-treated with 0.5 μM or 1 μM 2-methoxyestradiol and received 10 Gy radiation 12 hours later. Western blot analysis was then performed using p-SMAD, Smad 2/3, and alpha smooth muscle actin (α-SMA) antibodies. To measure a quantitative amount of the protein, Western blot was performed using β-actin antibodies. The results are shown in FIG. 6.

Figure 6:
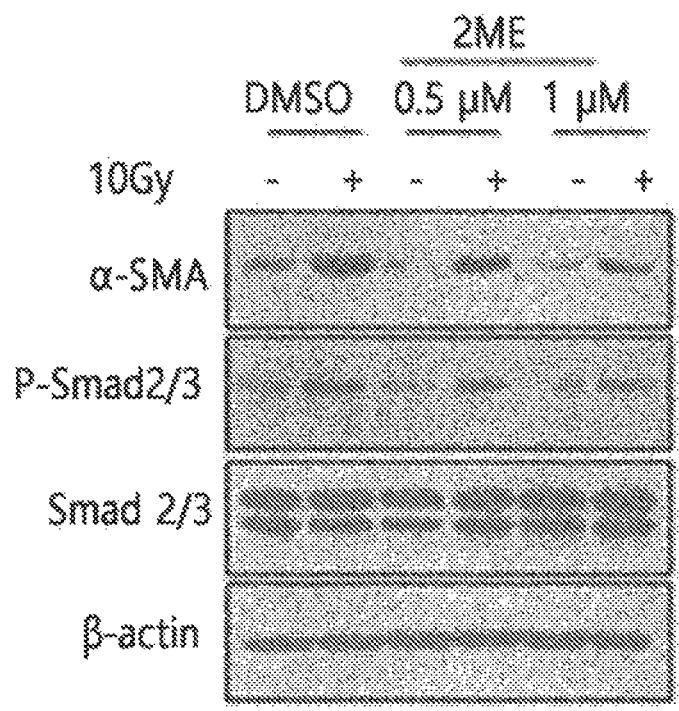
FIG. 6 shows the images showing the results of Western blot detecting changes in the expression of p-SMAD, Smad 2/3, and α-SMA, proteins related to HPAEC fibrosis, after the non-treatment or treatment with 2-methoxyestradiol and then irradiation.

FIG. 6 shows the images showing the results of Western blot detecting changes in the expression of p-SMAD, Smad 2/3, and α-SMA, proteins related to HPAEC fibrosis, after the non-treatment or treatment with 2-methoxyestradiol followed by irradiation.

According to FIG. 6, compared to the no-irradiation group, the group treated with 0.5 μM or 1 μM 2-methoxyestradiol showed a relative decrease in the p-SMAD, Smad 2/3, and α-SMA, proteins related to HPAEC fibrosis, at all concentrations; in particular, at the concentration of 1 μM.

Example 7

Fibrosis of Vascular Endothelial Cells Observed after Irradiation and Suppression Thereof Trp53<tm1Brn>/J and B6.129S4-Kras<tm4Tyj>/J were purchased from Jackson Laboratories (USA) and hybridized. Mice having mutated p53 and ras genes were obtained, and non-small cell lung cancer animal models were prepared (M*, Dooley A L*, Jacks T. 2009. Conditional mouse lung tumor models using adenoviral or lentiviral delivery of Cre recombinase. Nature protocols, 4(7): 1064-1072. PMCID: PMC2757265)).

The thus-obtained mouse model with lung cancer received 16 Gy radiation. The lung was extracted from the mouse, and was stained using the H&E staining or trichrome staining method, and the shape of pulmonary artery endothelial cells was then observed with a microscope. According to said staining method, the nucleus and cytoplasm were observed to be blue and pink, respectively. The group solely treated with 2-methoxyestradiol was intraperitoneally treated in an amount of 150 mg/kg. The group treated both with 2-methoxyestradiol and radiation was intraperitoneally treated with 2-methoxyestradiol in an amount of 150 mg/kg 1 hour before the irradiation. The result is shown in FIG. 7.

Figure 7:
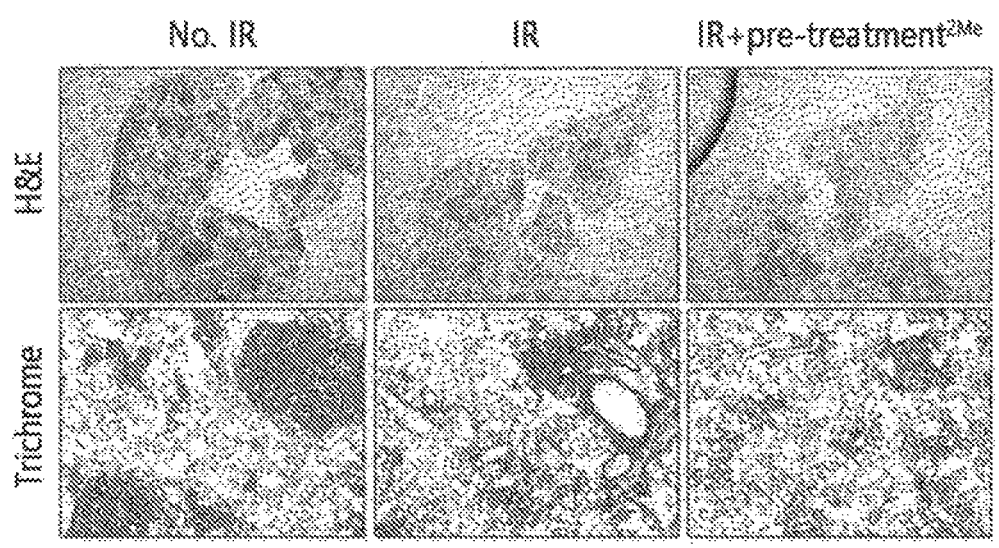
FIG. 7 includes photos of expression of collagen by not treating or treating the mouse model having lung cancer with 2-methoxyestradiol and irradiating the lung thereof followed by staining the pulmonary artery endothelium using a trichrome staining method, and photos of changes in the shape of the vascular endothelium tissue using an H&E staining method.

FIG. 7 includes photos of expression of collagen by not treating or treating the mouse model having lung cancer with 2-methoxyestradiol and irradiating the lung thereof, followed by staining the pulmonary artery endothelium using the trichrome staining method, and photos of changes in the shape of the vascular endothelium tissue using the H&E staining method. The black dashes represent the site of the lung cancer, and the white squares represent pulmonary arteries.

According to FIG. 7, the size of the tumor of the control group with no irradiation was reduced in the irradiation group (IR). Additionally, the irradiation group (IR) showed not only a reduced size of the tumor but also an increase in the collagen part (blue) around the vascular endothelium indicating pulmonary fibrosis. In contrast, the group pre-treated with 2-methoxyestradiol(IR+pre-treatment2Me) showed a significant decrease of the collagen stained in blue compared to the irradiation group (IR).

It can be understood from the result of FIG. 7 that 2-methoxyestradiol significantly suppressed the fibrosis of the HPAECs appearing as a side effect of radiotherapy for lung cancer.

While the present invention has been described with reference to the particular illustrative embodiments, it will be understood by those skilled in the art to which the present invention pertains that the present invention may be embodied in other specific forms without departing from its spirit or essential characteristics. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A radioprotection or radiomitigation method for radiation-induced damage, the method comprising administering a therapeutically effective amount of a compound of Formula 1 below, or a pharmaceutically acceptable salt thereof or a solvate thereof to an animal in need thereof:

[Formula 1]

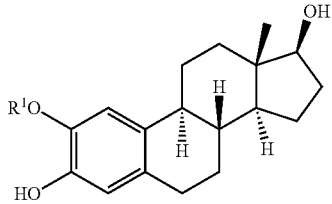

wherein, in Formula 1,
$R^1$ is hydrogen or $C_{1-3}$ alkyl.

2. The method of claim 1, wherein the compound of Formula 1 is 2-methoxyestradiol.

3. The method of claim 1, wherein the radiation-induced damage is vascular injury or skin damage due to radiation exposure.

4. The method of claim 1, wherein the radiation-induced damage is pulmonary fibrosis due to radiation exposure.

5. The method of claim 4, wherein the pulmonary fibrosis due to radiation exposure is a side effect induced by radiotherapy.

6. The method of claim 5, wherein the radiotherapy is for lung cancer, breast cancer, or Hodgkin's lymphoma.

7. The method of claim 1, wherein the radiation-induced damage is caused by radiation exposure, and the compound of Formula 1, the pharmaceutically acceptable salt thereof, or the solvate thereof is administered before or after the radiation exposure.

8. The method of claim 1, wherein the compound of Formula 1, the pharmaceutically acceptable salt thereof, or the solvate thereof is administered as an oral or an injectable preparation.

9. The method of claim 1, wherein the animal is a human.

10. The method of claim 1, wherein the pharmaceutically acceptable salt is a free acid salt.

11. The method of claim 10, wherein the free acid is an organic or an inorganic acid.

12. The method of claim 11, wherein the inorganic acid is hydrochloric acid, bromic acid or sulfuric acid.

13. The method of claim 11, wherein the organic acid is citric acid, acetic acid, lactic acid, tartaric acid, valeric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, or aspartic acid.

14. The method of claim 1, wherein the compound is administered within 3 weeks of radiation exposure, and the radiation-induced damage is occurred after 3 weeks of radiation exposure.

15. The method of claim 1, wherein the animal is suffering from lung cancer.

16. The method of claim 1, wherein the animal is a human.

* * * * *